United States Patent [19]

Roth

[11] 4,038,057

[45] July 26, 1977

[54] CLOSED CIRCUIT SAMPLER

[75] Inventor: Thomas P. Roth, Nashville, Tenn.

[73] Assignee: Andersen 2000, Inc., College Park, Ga.

[21] Appl. No.: 624,652

[22] Filed: Oct. 22, 1975

Related U.S. Application Data

[63] Continuation-in-part of Ser. No. 469,325, May 13, 1974, Pat. No. 3,922,905.

[51] Int. Cl.² .............................................. B01D 53/30
[52] U.S. Cl. ...................................... 55/270; 55/465; 73/28; 73/421.5 R
[58] Field of Search ...................... 55/270, 465; 73/28, 73/421.5 R; 195/127, 139

[56] References Cited

U.S. PATENT DOCUMENTS

3,001,914  9/1961  Andersen .................................. 73/28
3,795,135  3/1974  Andersen .................................. 73/28
3,922,905  12/1975  Roth ......................................... 73/28

Primary Examiner—Bernard Nozick
Attorney, Agent, or Firm—B. J. Powell

[57] ABSTRACT

A sampling device for removing particulate matter from a gaseous medium by jet impaction including a base, an impaction stage carried by the base and a connector diffuser carried by the impaction stage. The impaction stage has an apertured plate for generating a prescribed velocity of the gaseous medium as it passes therethrough, and a collection member is positioned under the apertured plate against which the gaseous medium impinges to collect the particulate matter thereon. Frangible locking means connect the jet impaction, the base stage and the connector diffuser together so that they cannot be separated without destruction of the locking means to prevent reuse.

10 Claims, 6 Drawing Figures

Fig 6

CLOSED CIRCUIT SAMPLER

CROSS-REFERENCE TO RELATED APPLICATIONS

This application is a continuation-in-part of my co-pending application Ser. No. 469,325, filed May 13, 1974 entitled "Disposable Sampler", now U.S. Pat. No. 3,922,905.

BACKGROUND OF THE INVENTION

There is a concern over the presence of particulate contaminates, especially viable particulate contaminates, in a respirable gaseous medium such as air. This has created a need to know if the gaseous medium contains contaminates and especially those contaminates which are respirable. Such a respirable gaseous medium may be simply the non-pressurized ambient atmosphere or the output of a positive pressure device. Numerous devices are used which generate a positive pressure outflow of a respirable gaseous medium such as inhalation or respiratory therapy equipment, anesthesia administration equipment and infant life support devices including incubators. Many of these devices also produce an aerosol entrained in the gaseous medium which aerosol serves as an ideal carrier for viable particles.

While a number of prior art air samplers are available for particle sampling of ambient air, none of these samplers are adapted to sample air or other gaseous mediums from a positive pressure delivery device such as those described above. Moreover, these prior art samplers must be reused in order to be economically feasible but this requires sterilization and additional handling between uses thereby increasing the likelihood of initial contamination of the sampler prior to the subsequent sampling operation. These prior art samplers have also used several stages which classified the air-borne particles into a like number of classes. In most instances, however, the information desired is whether the particles are sufficiently small to be inhaled and achieve lung penetration. The attempts to classify the particles as taught by the prior art into several classes has resulted in partial commingling of the classes so that the resulting readings were confusing.

SUMMARY OF THE INVENTION

These and other problems and disadvantages associated with the prior art are overcome by the invention disclosed herein by the provision of a simplified, inexpensive sampler construction which may be used to sample the gaseous medium output of positive pressure delivery devices and which reduces the initial capital cost thereof sufficiently to allow the sampler to be disposable and not be reused. The simplified construction of the sampler of the invention is such that it can be quickly and easily assembled and used by unskilled personnel without affecting the sampling capability of the sampling device. Further, the components of the sampler are locked together by a frangible locking means so that the locking means is destroyed as an incidense of the disassembly of the sampling device to prevent its reuse in a contaminated condition. This destruction of the locking means further provides a ready indication that the sampling device has been used to prevent the reassembly thereof in a contaminated state. The sampler is easily and simply connected to the gaseous medium output of a positive pressure delivery device for sampling. The sampler of the invention also incorporates a minimum number of components to facilitate the assembly and disassembly of the sampler as well as requiring the minimum amount of time to check the particles separated by the device. An adapter is also provided to allow the sampler to be used with a negative pressure device.

The invention, unlike the prior art, does not attempt to classify the impacted particles into several classifications, but simply into that class which can be inhaled. This gives both a simplified reading thereby requiring a minimum amount of time to check same.

The apparatus of the invention includes generally a base which defines an upwardly opening recess therein, a discharge outlet therefrom and a sealing flange formed around the outlet and flange, a jet stage which fits onto the base in sealing engagement with the sealing having frangible locking means to lock the jet stage onto the base in a sealed relationship therewith. A plurality of jet impaction passages are provided through the jet stage to selectively impact particles in the gaseous medium onto a collection member which may be selectively positioned on the base within the recess under the passages. A connector diffuser is carried on the jet stage in a sealing relationship therewith and defines an inlet passage therethrough. The connector diffuser is connectable to the gaseous medium output of a positive pressure delivery device so that the gaseous medium can be forced through the inlet passage in the connector diffuser, the jet impaction passages in the jet stage to impact particles in the gaseous medium onto the collection member, and then out through the discharge outlet in the base. An adapter is provided to alternatively connect the discharge outlet in the base to the inlet of a negative pressure device to force the gaseous medium such as the air surrounding the sampling device therethrough.

These and other features and advantages of the invention disclosed herein will become more apparent upon consideration of the following detailed description and accompanying drawings wherein like characters of reference designate corresponding parts throughout the several views and in which:

These figures and the following detailed description disclose specific embodiments of the invention; however, it is understood that the inventive concept is not limited thereto since it may be embodied in other forms.

DETAILED DESCRIPTION OF ILLUSTRATIVE EMBODIMENTS

Figure 3:
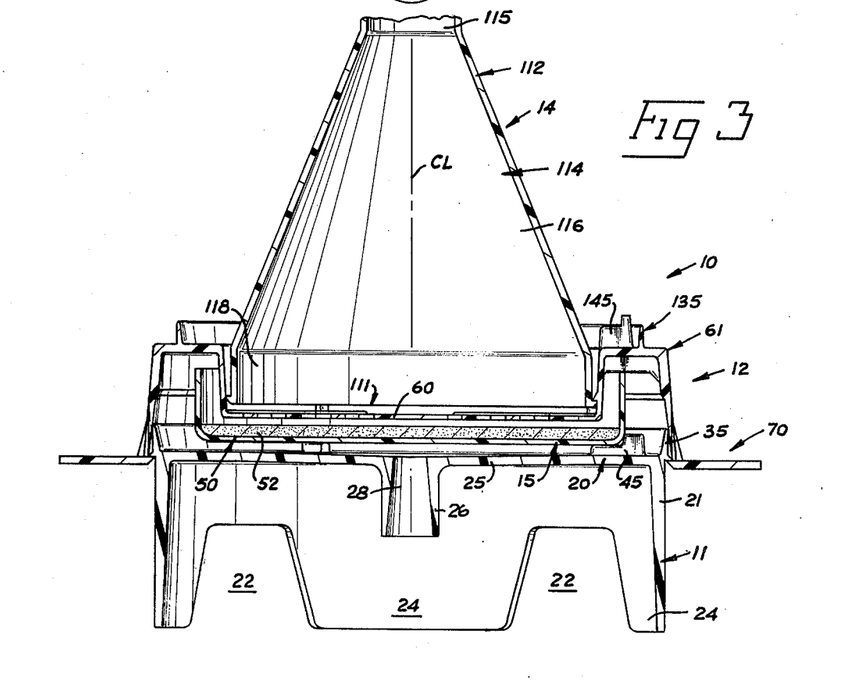
FIG. 3 is a cross-sectional view taken along line 3—3 in FIG. 2.

Referring to the figures, it will be seen that the sampler 10 comprises generally a base 11, a jet stage 12 mounted on top of the base 11, and a connector diffuser 14 mounted on top of the jet stage 12. A collection member 15 as best seen in FIG. 3 is carried by the base 11 under the jet stage 12 so that the entrained particles from the gaseous medium being sampled are impinged thereon by the jet stage. The base 11, jet stage 12 and connector diffuser are made of resilient plastic. The gaseous medium which is to be sampled is forced through the connector diffuser 14 and the jet stage 12 against the collection member 15, then around the collection member 15, and subsequently out through the base 11. While any gaseous medium may be sampled, the sampler 10 is especially useful in sampling a breathable mixture from the pressurized outlet tube T seen in FIG. 1 when it is placed on the connector diffuser 14.

The base 11 as best seen in FIG. 3 includes generally a circular web 20 from which depends an annular support flange 21 with appropriate cutouts 22 formed therein to define support legs 24 on the flange 21 to support the base 11 in an upright position on an appropriate surface. The circular web 20 includes a slightly conical central portion 25 in the center of which is provided an outlet tube 26 defining an outlet passage 28 therethrough. The outlet passage 28 is sized so the gaseous medium flowing out of the sampler is not significantly restricted.

Figure 4:
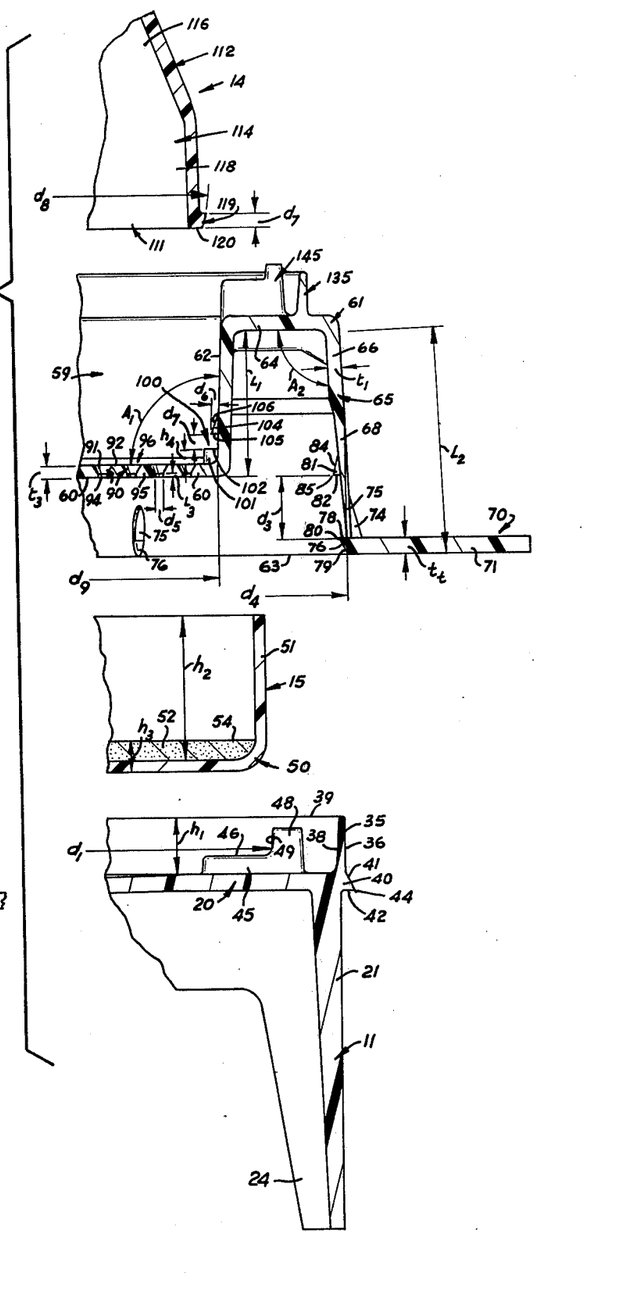
FIG. 4 is a partial cross-sectional exploded view taken along line 3—3 in FIG. 2.
Figure 5:
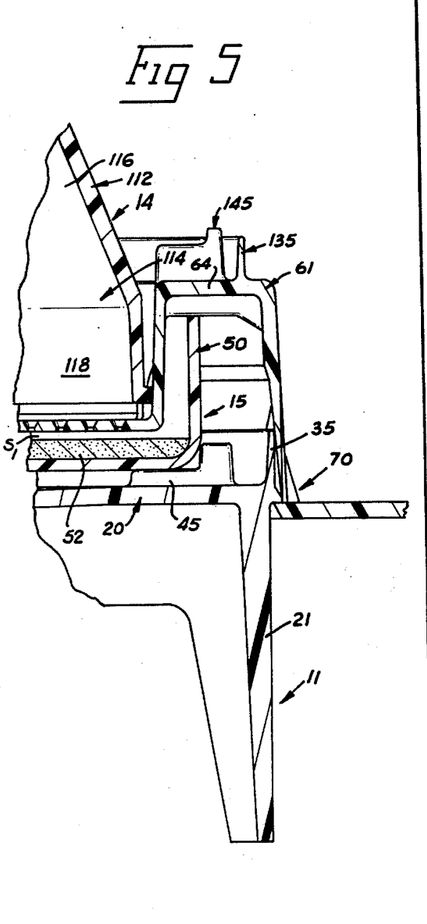
FIG. 5 is an enlarged partial cross-sectional view taken similarly to FIG. 4 showing the connection between the connector diffuser and the jet stage; and, FIG. 6 is a cross-sectional view similar to FIG. 3 showing a modification of the invention adapted to be operated by a vacuum source.

An upstanding endless annular sealing flange 35 as best seen in FIGS. 4 and 5 is provided adjacent the outside upper edge of the circular web 20 which has a generally vertical outer sealing face 36, an inner face 38 and an upper edge 39 which lies in a plane generally normal to the centerline CL of sampler 10 and concentrically thereabout. The sealing flange 35 has a height $h_1$ to contact the jet stage 12 as will become more apparent. The outer circular edge of the circular web 20 is provided with an endless locking lip 40 which projects outwardly from the base of the sealing flange 35. The locking lip 40 defines an inwardly tapering upper guide surface 41 and a lower generally horizontal locking surface 42 which intersects the upper guide surface 41 to form a relatively sharp edge 44 as best seen in FIGS. 4 and 5. The locking lip 40 is designed to engage and lock the jet stage 12 onto the base 11 as will be more fully explained.

Circumferentially spaced about the upper surface of the circular web 20 inside the sealing flange 35 are a plurality of upstanding locators 45 seen in FIGS. 4 and 5 which support and locate the collection member 15 thereon. Each of the locators 45 defines an inside upwardly facing, radially extending support surface 46 and an upstanding positioning tab 48 at the outer end of each of the support surfaces 46. The inside edges 49 of the upstanding positioning tabs 48 are located along a circle concentric with about the centerline CL of the sampler 10 and base 11 with a diameter $d_1$ so that the collection member 15 will be supported by the surfaces 46 and located by the inside edges 49 of the tabs 48. It will be further noted that the inside supporting surfaces of the locators 45 lie in a common plane generally normal to centerline CL as will become more apparent.

The collection member 15 illustrated is for use primarily to collect viable samples, however, it is to be understood that alternate collection members may be substituted for member 15 when collecting non-viable samples. The member 15 is a standard petri dish 50 as best seen in FIGS. 3-5 which have an outside diameter substantially equal to the diameter $d_1$ of the circle defined by the inside edges 49 of tabs 48. Each of the petri dishes 50 has an upstanding annular side wall 51 with a height $h_2$ as will become more apparent. An agar layer 52 is provided in petri dish 50 that has a nutrient material mixed therein to incubate viable organisms on the nutrient mixture. The layer 52 has an upper impaction surface 54 onto which the jet impaction passages impinge the gaseous medium as will become more apparent. The dish 50 is filled with layer 52 to a standard height so that surface 54 is located a prescribed distance $h_3$ from the bottom surface of dish 50 as will be more fully explained. Thus, when collection member 15 is placed on locators 45, it is centered about centerline CL and supported so that the impaction surface 54 has a known location generally normal to centerline CL.

The jet stage 12 is adapted to fit on the base 11 so as to overlie the collection member 15. Stage 12 as seen in FIGS. 3-5 includes a central circular apertured plate 60 joined to an annular inverted U-shaped flange 61 around its periphery so as to define an upwardly opening recess 59 above plate 60. The annular inside leg 62 of flange 61 is integral along its lower edge with the peripheral edge of plate 60 and extends upwardly therefrom with a prescribed obtuse angle $A_1$ seen in FIG. 4 defined between leg 62 and plate 60 so that leg 62 flares slightly outwardly about plate 60. The flange 61 as best seen in FIGS. 4 and 5 has an annular central web 64 oriented generally parallel to plate 60 and integral with the upper end of inside leg 62 along the inside edge of web 64. An annular outside positioning leg 65 of flange 61 is integral with the outside edge of central web 64 and depends therebelow defining an obtuse angle $A_2$ with web 64. The inside leg 62 as seen in FIG. 4 has a length $L_1$ while the outside leg 65 has a longer length $L_2$ as seen in FIG. 4 so that the lower edge 63 of leg 65 lies below the plane of leg 62 as will become more apparent.

Figure 1:
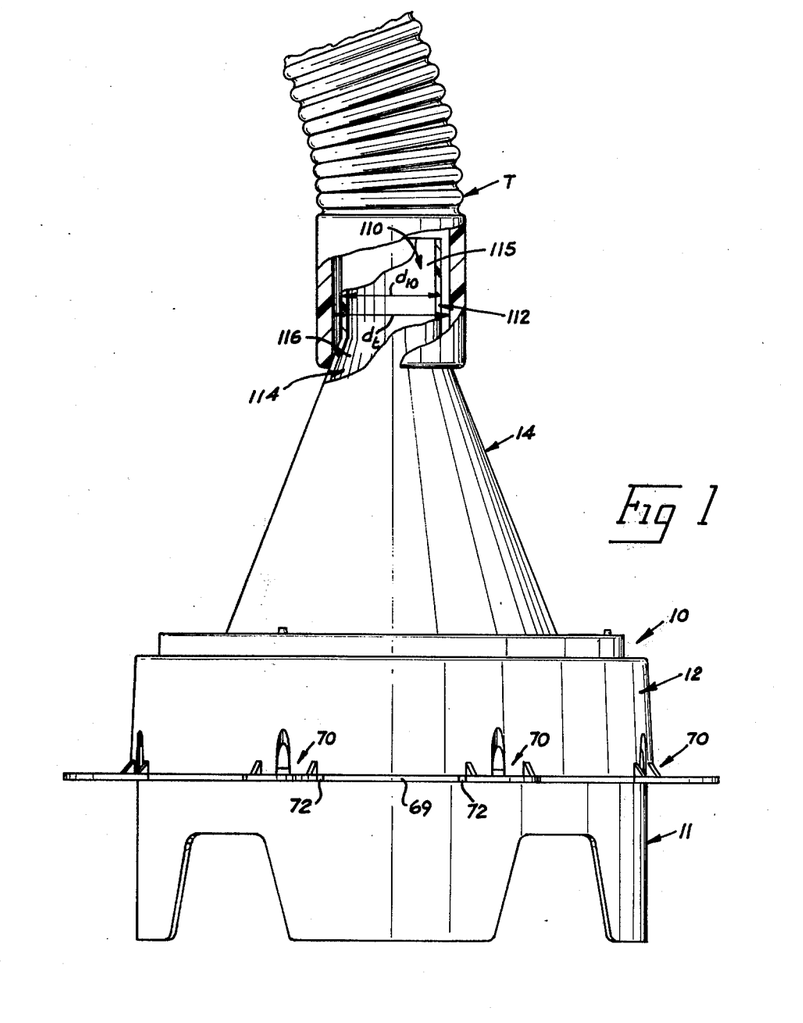
FIG. 1 is a side view of the invention in use.

The outside leg 65 has a first thickness $t_1$ at its upper portion seen in FIG. 4 to define an upper annular section 66 and a thinner tapering portion below section 66 to define a frangible section 68. An upwardly facing reinforcing lip 69 as best seen in FIGS. 1 and 2 is provided around the lower extending edge of the section 68 as will be more fully explained.

Figure 2:
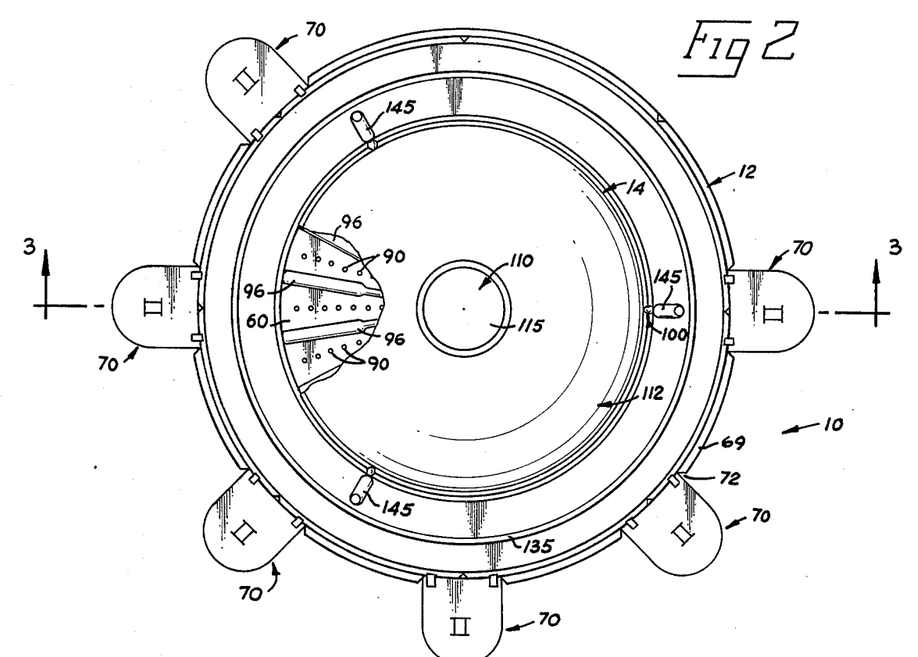
FIG. 2 is a top plan view of the invention of FIG. 1.

Circumferentially spaced about the lower edge of section 68 are a plurality of locking assemblies 70 seen in FIGS. 1-5 which selectively lock the jet stage 12 onto the base 11. Each of the locking assemblies 70 includes a manually engagable breakoff tab 71 with a prescribed thickness $t_t$ seen in FIG. 4 adapted to be manually engaged as hereinafter explained to remove the jet stage 12 from the base 11. Each of the breakoff tabs 71 is located in the plane of the reinforcing lip 69 normal to centerline CL. A cutout 72 as seen in FIG. 2 is provided in the reinforcing lip 69 on opposite sides of the breakoff tab 71 to reduce the strength thereof as will become more apparent. Each of the breakoff tabs 71 is joined to the frangible section 68 of the leg 65 at its inside end and a pair of reinforcing ribs 74 seen in FIGS. 2 and 4 integral with both the breakoff tabs 71 and the frangible section 68 further connect the tab 71 to the frangible section 68. An inverted V-shaped cutout 75 as seen in FIG. 4 is provided through the frangible section 68 centrally of each of the tabs 71 with its bottom edge terminating in the plane of the upper surface of the tab 71. Directly behind the V-shaped cutout 75 at its lower end is an inwardly projecting locking protuberance 76 seen in FIG. 4 which defines a locking surface 78 on the upper end thereof lying generally in the plane of the surface of the breakoff tab 71 and a downwardly and outwardly tapered guide surface 79 that extends from the inside corner 80 of the upper locking surface 78 to terminate at the inside surface of the lower edge of the breakoff tab 71. Spaced a prescribed distance $d_3$ seen in FIG. 4 above the locking surface 78 of each of the locking protruberances 76 is a positioning abuttment 81 generally aligned with the locking protruberance 76. The positioning abutment 81 defines a bottom abutment surface 82 which faces the upper locking surface 78 of locking protruberance 76 and is generally parallel thereto. The abutment surface 82 is spaced above the upper locking surface 78 of locking protruberance 76 the prescribed distance $d_3$. An upwardly and outwardly tapered surface 84 joins the inside corner 85 of abutment surface 82 with the inside of the frangible section 68 of leg 65. The inside diameter $d_4$ seen in FIG. 4 of the frangible section 68 immediately above the upper locking surface 78 of locking protruberance 76 is substantially equal to the outside diameter of the sharp edge 44 of locking lip 40 as will become more apparent.

Thus, it will be seen that as the jet stage 12 is placed over the upstanding sealing flange 35 of the base 11 and pushed toward the base 11, the tapered inside guide surfaces 79 of the locking protruberances 76 will deflect the locking protruberances 76 outwardly and enlarge the diameter of the frangible section 68 sufficiently to allow the locking protruberances 76 to pass over the sharp edge 44 on the locking lip 40. Once the locking protruberances 76 pass over the locking lip 40, the resiliency of the frangible section 68 of leg 65 causes the locking protruberances 76 to snap back into position under the locking lip 40 so that the upper locking surfaces 78 of the locking protruberances 76 pass immediately under the lower locking surface 42 of the locking lip 40 as seen in FIG. 5. At the same time, the abutment surfaces 82 of the positioning abutments 81 engage the upper edge 63 of the sealing flange 35 so that the jet stage 12 is positively locked into position by the positioning abutments 81 engaging the sealing flange 35 and the locking protruberances 76 engaging the locking lip 40 as seen in FIG. 5. Because the distance $d_3$ is substantially equal to the distance between the lower locking surface 42 of the locking lip 40 and the upper edge of the sealing flange 35, it will be seen that the stage 12 is positively positioned. While the frangible section 68 of leg 65 is sufficiently resilient to allow the tapered guide surfaces 79 on locking protruberances 76 to expand the section 68 sufficiently outwardly to pass over the locking lip 40 on base 11, the upper locking surfaces 78 on the locking protruberances 76 in conjunction with the lower locking surface 42 on the locking lip 40 prevents the disassembly of the jet stage 12 from the base 11 without fracturing the frangible section 68 of the leg 65. When it is desirable to remove the jet section 12 from the base 11, the breakoff tabs 71 are manually engaged and the outer ends thereof are pivoted upwardly toward the leg 65 to cause the leg 65 to fracture about the breakoff tabs 71. Because the locking protruberances 76 are carried by the breakoff tabs 71, they are removed therewith. When the locking protruberances 76 are removed, the jet stage cannot be relocated on base 11 and locked in position. This ensures that the sampler 10 will not be reused in a contaminated state.

It will further be noted that when the locking protruberances 76 snap under the locking lip 40 on base 11, the outer sealing face 36 of the sealing flange 35 on base 11 engages the inside surface of the frangible sections 68 to seal the same as seen in FIG. 5. This is because the inside surface of the frangible section 68 flares outwardly while the sealing face 36 of flange 35 extends generally vertically. This forms a positive seal between the base 11 and the jet stage 12 to define a sealed chamber 86 best seen in FIG. 3 between the base 11 and the jet stage 12 with a space S seen in FIG. 5 around the side wall 51 of the dish 50 to allow the gaseous medium to pass from the impaction surface 54 of the member 15 over the side wall 51 thereof, then outwardly around the dish 50 and under the dish 50 between the locators 45 so that the gaseous medium can be forced out of the chamber 86 through the outlet passage 28.

The central plate 60 defines a plurality of jet impaction passages 90 seen in FIGS. 2-5 therethrough arranged along radially extending paths with respect to the plate 60 and also along concentric circular paths about the centerline CL. Each of the jet impaction passages 90 defines a countersunk approach section 91 seen in FIG. 4 that opens onto the upper surface 92 of plate 60 at its large end and a cylindrical substantially constant diameter jet section 94 which extends from the lower end of the countersunk approach section 91 to the bottom surface 95 of plate 60. The countersunk approach section 91 serves to reduce the turbulence and enhance the laminar flow through the jet section 94 of the passages 90 to obtain better impacting characteristics of the air-borne particles in the gaseous medium passing therethrough. While the diameters of the jet sections 94 of the passages 90 may be varied to suit the particular circumstances, the diameter $d_5$ illustrated in FIG. 4 is 0.0166 inch. The thickness $t_3$ of the plate 60 is 0.040 inch while the length $L_3$ of the jet section 94 is 0.020 inch. The particular countersunk approach section 91 is a 60° countersink. The space $s_1$ been in FIG. 5 between the bottom surface 95 of the plate 60 and the impaction surface 54 on the collection member 16 is 0.050 inch. The arrangement of the locators 45, the locking lip 40, the locking protruberances 76, the abutment surfaces 82, and the plate 60 are such to ensure this spacing will be produced when a standard petri dish 50 is placed on the locators 45 and is prefilled with the agar layer to a standard height. It will further be noted that there are 200 of the passages 90 in the plate 60 illustrated. A plurality of radially extending reinforcing ribs 96 located on the upper surface 92 of plate 60 as seen in FIG. 4 bisect the space between radial paths along which the passages 90 are located and serve to both reinforce plate 60 and act as a flow dividing mechanism to separate the flow of the gaseous medium passing to the passages 90 in the plate 60.

Located at circumferentially spaced positions on the inside leg 62 of the jet stage 12 within the recess 59 are a plurality of positioning assemblies 100 one of which is seen in FIGS. 4 and 5 which serve to connect the connector diffuser 14 to the jet stage 12. While different numbers of assemblies 100 may be used, three are incorporated in the sampler illustrated. Each of the assemblies 100 includes a spacer 101 integral with the inside leg 62 and plate 60 at their juncture and which projects out into recess 59 defining an upper support surface 102 thereon generally normal to centerline CL. The support surface 102 is located a prescribed height $h_4$ above the upper surface 92 of plate 60 as seen in FIG. 4. The lower end of the connector diffuser 14 engages the spacers 100 to locate same as will become more apparent. Each of the assemblies 100 also includes a catch 104 seen in FIG. 4 located on the inside leg 62 directly above the spacer 101. The catch 104 projects out into recess 59 a prescribed distance $d_6$, and has a lower catch surface 105 generally normal to the centerline CL and located a prescribed distance $d_7$ seen in FIG. 4 above surface 102 on spacer 101. Catch 104 also has a deflecting surface 106 which angles inwardly and downwardly from leg 62 to join with the catch surface 105. The catch 104 serves to positively position the connector diffuser 14 as will become more apparent.

The connector diffuser 14 is a cone shaped member which fits onto the jet stage 12 in a sealing relationship therewith so that the outlet tube T from a positive pressure producing device can be connected thereto and force the gaseous medium through the sampler to sample the gaseous medium. The connector diffuser 14 as best seen in FIGS. 1 and 3-5 has an inlet 110 at its upper end and an outlet 111 at its lower end with a tubular side wall 112. The side wall 112 defines a passage 114 therethrough with a generally cylindrical inlet section 115 at its upper end, an outwardly flaring intermediate section 116 integral with the lower end of section 115, and a generally cylindrical section 118 integral with the lower end of section 116. Therefore, it will be seen that the passage 114 diverges from the upper to the lower end of the connector diffuser 14.

The lower end of the side wall 112 has an outwardly projecting bead 119 thereon around the outside thereof. The bead 119 is integral with side wall 112 so that the lower surface 120 of bead 119 is at the bottom of side wall 112 and oriented generally normal to the centerline CL. The bead 119 has an upper locking surface 121 thereon spaced above the lower surface 120 the same distance $d_7$ as that between spacer 101 and catch 104 and oriented generally normal to the centerline CL of the sampler. The bead 119 also has an edge surface 122 which joins surfaces 120 and 121 and angles upwardly and outwardly from its juncture with surface 120. The sharp edge 124 between edge surface 122 and upper surface 121 has a diameter $d_8$ slightly greater than the diameter $d_9$ of the inside surface of leg 62 on stage 12 immediately below the catch 104 so that a seal will be formed between stage 12 and connector diffuser 14 as will become more apparent.

The side wall 112 at the inlet section 115 has an outside diameter $d_{10}$ best seen in FIG. 1 which is at least as small as the minimum inside diameter $d_t$ of the tubing T with which the sampler 10 is to be used. If the inside diameter $d_t$ is larger than the diameter $d_{10}$, the tubing T is simply inserted over the inlet section 115 until the end of the tubing T engages the side wall 112 at the outwardly flaring intermediate section 114 as seen in FIG. 1 and forms a seal between the tubing T and the connector diffuser 14.

It will also be noted that the jet stage 12 may have a sealing flange 135 formed on the top thereof as best seen in FIG. 4 where the sealing flange 135 is located on the central web 64 of U-shaped flange 61 and projects upwardly therefrom. The sealing flange 135 has a configuration similar to the flange 35 and serves a similar function as the flange 35 if it is desirable to add additional jet stages to the stage 12. Appropriate locators 145 may be provided on the central web 64 of the stage 12 inside the sealing flange 135 to properly position other petri dishes or collection members associated with the upstream jet stage so that particles may be sized and impacted in the petri dish from the upstream jet stages carried on the jet stage 12.

Figure 6:
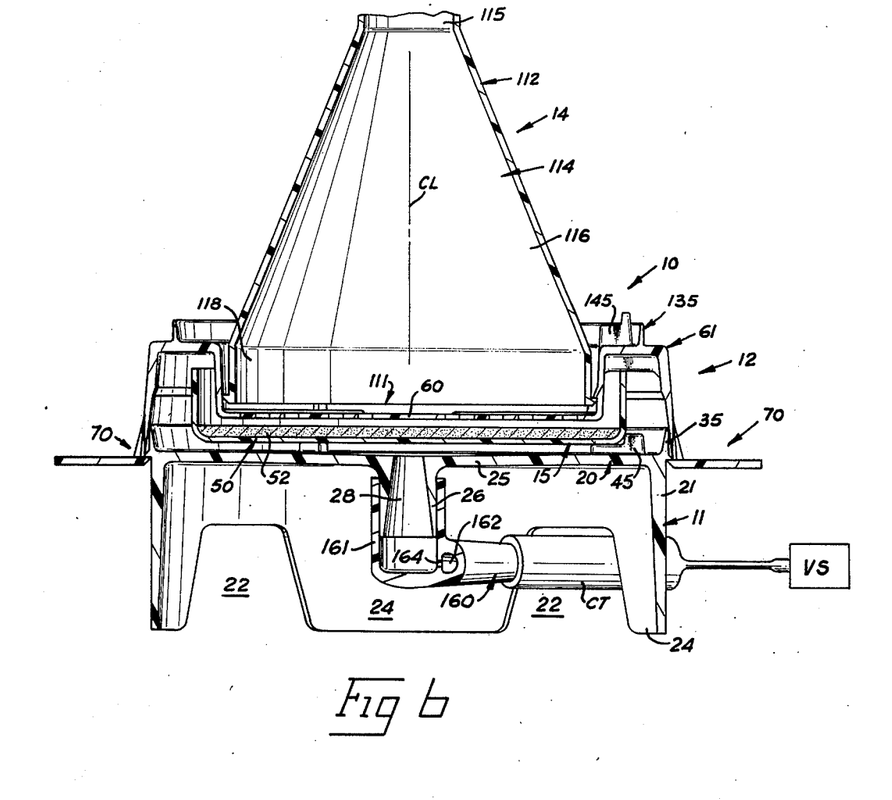

In some instances, it may be desirable to sample a non-pressurized gaseous medium such as ambient air to see if it contains particulate contaminates. FIG. 6 shows an adaptor which may be applied to the outlet tube 26 and connected to a vacuum source VS through connecting tubing CT to sample such non-pressurized gaseous mediums. The adaptor 160 is made out of a resilient plastic material with an inlet passage 161 therein sized to fit over and seal the outlet tube 26 so that the gaseous medium passing out of the outlet tube 26 through the passage 28 passes into the adaptor 160. The adaptor 160 further includes an outlet passage 162 which communicates through the connecting tubing CT to the vacuum source VS. An orifice 164 is defined between the inlet passage 161 and outlet passage 162 and serves to regulate the flow of the gaseous medium therethrough. Usually, this orifice 164 would be a critical size orifice so that the vacuum imposed in the sampler 10 through the passage 28 may vary without the flow rate of the gaseous medium through the sampler 10 varying. When the adaptor 160 is used, the connector diffuser 14 may be left off of the stage 12 so that free access of the gaseous medium to the stage 12 is permitted. In some instances, it may be desirable to leave the connector diffuser 14 in place for the sampling operation.

ASSEMBLY AND OPERATION

The sampler 10 is assembled by placing the base 11 in an upright position and then placing the standard petri dish 50 or other collection member 15 on the locators 45 so that the collection surface 54 thereof faces upwardly. If the petri dish is provided with a lid, this lid should be removed. Next, the jet stage 12 is placed over the base 11 so that the outside leg 65 extends over the extending sealing flange 35 and the jet stage 12 is forced downwardly so that the locking protruberances 76 on the inside of the legs 65 are deflected outwardly and over the locking lip 40 on the base 10 and the locking protruberances 76 snap back under the locking lip 40 to lock the jet stage 12 onto the base 11 with the abutments 81 engaging the top of the sealing flange 35. This properly spaces the jet impaction passages 90 with respect to the collection surface 54 as seen in FIG. 5. Next, the lower end of the connector diffuser 14 is placed inside the recess on jet stage 12 and the connector diffuser pressed downwardly so that the bead 119 is deflected inwardly by the catches 104 since the lower section of the side wall 112 is sufficiently resilient to be deflected inwardly and the bead 119 snaps back out under the catches 104 while the lower surface 120 of the bead 119 rests on the spacers 101. The sampler 10 is now ready for use. The outlet tube T of the positive pressure equipment being tested is inserted over the upper inlet end of the connector diffuser 14 as seen in FIG. 1 and pressed down against the connector diffuser 14 to form a seal between the tube T and the connector diffuser 14. As a gaseous medium being discharged from the tube T passes through the jet stage 12, the passages 90 cause the particles in the gaseous medium to be impacted onto the surface 54 of the agar layer 52 in the dish 50. When sampling for a prescribed period of time has been completed, the tabs 71 are forced upwardly to break the frangible section 68 of the legs 65 and remove the locking protruberances 76 from engagement under the locking lip 40 on the base 11. This allows the jet stage 12 to be removed from the base 11 and the petri dish 50 removed and incubated.

I claim:

1. A sampling device for separating entrained particles from the pressurized gaseous medium output of a positive pressure device, the positive pressure device having an outlet tube with a prescribed diameter discharge opening therein from which the pressurized gaseous medium output is discharged, said sampling device comprising:

an impaction member including a generally circular jet plate and a seamless annular resilient impaction sealing flange integral with said jet plate about the periphery thereof, said jet plate having an impaction centerline, an upstream side, a downstream side and a prescribed plate diameter larger than the diameter of the discharge opening in the outlet tube, said impaction member defining a plurality of jet impaction passages therethrough to direct the gaseous medium along spaced paths generally parallel to said first centerline from the upstream side of said impaction member to the downstream side of said impaction member to divide the flow of the gaseous medium into a plurality of impaction jet streams, said annular impaction sealing flange concentric about said impaction sealing flange and extending away from the upstream side of said jet plate, said impaction sealing flange further defining an inside outwardly flaring impaction sealing surface concentric about said impaction centerline increasing in diameter in a direction away from the upstream side of said jet plate;

a collection member means positioned adjacent the downstream side of said jet plate and defining a collection surface thereon facing the downstream side of said jet plate so that the impaction jet streams will be directed against the collection surface on said collection member means and at least a portion of the particles of a prescribed diameter range entrained in the gaseous medium will be jet impacted onto the collection surface of said collection member means;

a base support member positioning said collection member means with respect to said jet impaction passages so that said collection surface is generally parallel to the downstream surface of said jet plate and operatively associated with said jet impaction passages to cause the particles in the gaseous medium to be jet impacted onto said collection surface as the gaseous medium is forced through said jet impaction passages, said base support member having a support centerline coaxially aligned with said impaction centerline, and defining a base support outlet therethrough through which the gaseous medium passes after impaction against the collection member;

a connector-diffuser member having a diffuser centerline, an inlet end and a discharge end operatively associated with said impaction member for placing said jet impaction passages in said impaction member in communication with the pressurized gaseous medium output of said positive pressure device so that the gaseous medium output is forced through said jet impaction passages by said positive pressure device to cause the entrained particles in said pressurized gaseous medium to be jet impacted onto said collection member whereupon the gaseous medium passes out of said sampling device through said base support outlet, said connector diffuser member including an annular seamless diffuser side wall defining a diversing central diffuser passage therethrough which diverges from the inlet end to the discharge end of said connector-diffuser member, said inlet end defining an inlet opening therein to said central diffuser passage smaller in diameter than the discharge opening in the outlet tube of the positive pressure device so that the outlet tube can be pressed onto the inlet end of said connector-diffuser member to seal the outlet tube to the inlet end of said connector-diffuser member and place the discharge opening in the outlet tube in sealed communication with said diffuser passage in said connector-diffuser member through the inlet opening thereto, said discharge end defining an outlet opening therein from said central diffuser passage, said connector-diffuser member including a resilient, outwardly projecting sealing bead integral with said diffuser side wall at the discharge end thereof, said sealing bead concentric about said diffuser centerline and defining a seamless bead sealing surface thereon outboard of said diffuser side wall, said bead sealing surface having an outside diameter larger than the smallest diameter of said impaction sealing surface but smaller than the largest diameter of said impaction sealing surface so that when the discharge end of said connector-diffuser member is forced toward the upstream side of said jet plate of said impaction member with the diffuser centerline coaxial with the impaction centerline, said bead sealing surface on said connector-diffuser member will sealingly engage said impaction sealing surface of said impaction sealing flange on said impaction member to seal the outlet opening from said connector-diffuser member to the upstream side of said jet plate of said impaction member; and, locking means for maintaining said sealing bead on said connector diffuser member in sealing engagement with said impaction sealing flange on said impaction member, said locking means including first resilient catch means carried by the discharge end of said connector-diffuser member and second resilient catch means carried by said impaction member, said first and second resilient catch means constructed and arranged to be resiliently deflected past each other as the discharge end of said connector-diffuser member is forced toward the upstream side of said jet plate and to resiliently snap back into interference with each other when said sealing bead is in sealing relationship with said impaction sealing flange to lock said connector-diffuser member onto said impaction member in a sealed relationship therewith so that when the discharge opening in the outlet tube from the positive pressure device is sealingly pressed onto the inlet end of said connector-diffuser member, the pressurized gaseous medium output from the positive pressure device will be forced through said diffuser passage in said connector-diffuser member, then through the the impaction passages in said impaction member against said collection member means to cause at least a portion of the particles of a prescribed diameter range entrained in the gaseous medium to be jet impacted onto the collection surface of said collection member means and thus separated from the gaseous medium, and then out of the sampling device through said base support outlet.

2. A sampling device for alternative connection to a positive pressure device having a positive pressure outlet of a prescribed discharge diameter and to a negative pressure device having a negative pressure inlet for separating particles from entrainment in a gaseous medium passing through said sampling device by jet impaction alternatively from the positive pressure device and the ambient atmosphere comprising:

an impaction member having a first centerline, an upstream side and a downstream side, said impaction member defining a plurality of jet impacton passages therethrough to direct the gaseous medium along spaced paths generally parallel to said first centerline from the upstream side of said impaction member to the downstream side of said impaction member to divide the flow of the gaseous medium into a plurality of impaction jet streams;

a collection member defining a collection surface thereon onto which the entrained particles in the gaseous medium are to be impacted;

support member means connected to the downstream side of said impaction member in a sealed relationship therewith and positioning said collection member with respect to said jet impaction passages so that said collection surface is operatively associated with said impaction passages to cause the impaction jet streams to be directed against said collection surface and at least a portion of the particles entrained in the gaseous medium to be jet impacted onto said collection surface, and separated from the gaseous medium, said support member defining an outlet opening therefrom downstream of said collection member through which the gaseous medium passes after the particles are jet impacted onto said collection member;

a connector-diffuser member having an inlet end and a discharge end alternatively and selectively connectable with said impaction member in a sealed relationship with the upstream side of said impaction member for alternatively placing said jet impaction passages in said impaction member in communication with a positive pressure device so that the gaseous medium from the positive pressure outlet of the positive pressure device is forced through said connector-diffuser member and said jet impaction passage by said positive pressure device to cause at least a portion of the particles entrained in the gaseous medium flowing through said jet impaction passages to be impacted onto said collection surface by jet impaction and separated from the gaseous medium, said connector-diffuser member defining an inlet opening at the inlet end thereof smaller in diameter than the discharge diameter of the positive pressure outlet from the positive pressure device so that the positive pressure outlet can be pressed onto the inlet end of said connector-diffuser member to seal the positive pressure outlet to the inlet end of said connector-diffuser member and place the positive pressure outlet in sealed communication with said inlet opening in said connector-diffuser member to direct the gaseous medium from the positive pressure outlet through said connector-diffuser member and said jet impaction passages in said impaction member onto said collection surface on said collection member and then out through said outlet opening in said support member;

resilient locking means for permitting said connector-diffuser member to be forced into sealing engagement with the upstream side of said impaction member and for preventing said connector-diffuser member from being removed from sealing engagement with said impaction member once sealing engagement is achieved; and, flow control means alternatively connectable to said outlet opening in said support member when said connector-diffuser member is not in sealing engagement with said impaction member for connection to the negative pressure inlet of the negative pressure device so that said negative pressure device alternatively causes a negative pressure to be imposed through said sampling device to cause the gaseous medium from the ambient atmosphere to be drawn through said jet impaction passages in said impaction member so that the gaseous medium is jet impacted onto said collection surface of said collection member and separates at least a portion of the entrained particles in the gaseous medium on the collection surface by jet impaction, said flow control means defining a critical size orifice therein through which the gaseous medium passes to said negative pressure device from said support member after impaction on said collection surface to generate a substantially constant flow of the gaseous medium through said sampling device when said negative pressure device imposes a negative pressure on said outlet opening in said support member above a minimum prescribed value.

3. The sampling device of claim 1 wherein said impaction member further includes a plurality of connector abuttment members carried by said impaction member at the upstream side of said jet plate, each of said connector abuttment members defining a connector abuttment surface thereon, said connector abuttment surfaces lying in a common plane generally perpendicular to said impaction centerline and adapted to engage said connector diffuser member at the discharge end thereof to locate said connector-diffuser member so that said diffuser centerline is coaxial with said impaction centerline, said abuttment surfaces located with respect to said second resilient catch means of said locking means so that said connector-diffuser member is supported on said abuttment surfaces when said first and second resilient catch means are in their locked position to positively locate said connector-diffuser member with respect to said impaction member.

4. The sampling device of claim 3 wherein said sealing bead forms said first resilient catch means of said locking means.

5. The sampling device of claim 4 wherein said second resilient catch means of said locking means includes a plurality of connector catch members mounted on said impaction sealing flange and operatively associated with said connector abuttment members to engage said sealing bead on said connector-diffuser member when said connector-diffuser member is supported on said connector abuttment members to positively locate said connector-diffuser member with respect to said impaction member.

6. The sampling device of claim 5 wherein said annular seamless tubular diffuser side wall of said connector-diffuser member includes a generally cylindrical inlet section at the inlet end of said connector-diffuser member having an inlet outside diameter smaller than the prescribed diameter of the discharge opening from the outlet tube of the positive pressure device, an outwardly flaring intermediate section integral with said inlet section, said intermediate section having a first intermediate outside diameter at that end integral with said inlet section substantially equal to the inlet outside diameter of the inlet section and a second intermediate outside diameter larger than said first intermediate diameter but smaller than the diameter of said bead sealing surface on said sealing bead, and a generally cylindrical resilient discharge section integral with that end of said intermediate section opposite said inlet section, said discharge section having a diameter substantially equal to said second intermediate diameter and mounting said sealing bead thereon.

7. The sampling device of claim 6 wherein each of said connector catch members defines an inwardly angled, deflection surface and a lower catch surface thereon, said lower catch surface generally normal to said impaction centerline and spaced a prescribed catch distance above said abutment surface on said abutment member associated therewith; and wherein said sealing bead defines a lower abutment surface thereon generally normal to said diffuser centerline and, an upper locking surface thereon spaced above said lower surface at substantially the same prescribed distance as the catch distance between said catch surface on said catch members and said abutment surface on said abutment members, and wherein said bead sealing surface joint said lower abutment surface and said upper locking surface and angles upwardly and outwardly from its junction with said lower abutment surface so that said bead sealing surface deflects said bead inwardly past said catch members as said connector-diffuser member is forced toward said abutment members, said bead having a resiliency such that said upper locking surface is urged under said lower catch surfaces on said catch members after said bead passes said catch members.

8. The sampling device of claim 7 further including frangible means operatively connecting said impaction member and said support member together, said frangible means constructed and arranged to be destroyed as an incident to the separation of said impaction member and said support member to prevent reassembly thereof and including first locking means and second locking means adapted to engage each other to maintain said impaction member and said support member in a sealed relationship with each other, said first locking means being frangible so that disengagement of said first locking means from said second locking means fractures said first locking means to prevent re-engagement of said first locking means with said second locking means to reconnect said impaction member and said support member together.

9. The sampling device of claim 8 wherein said impaction member includes an inverted generally U-shaped annular flange integral with the periphery of said jet plate, said impaction sealing flanges forming the inside depending annular leg of said U-shaped flange, said U-shaped flange further having an outside depending leg mounting said first locking means of said frangible means thereon to connect said impaction member to said support member.

10. The sampling device of claim 1 further including flow control means removably connected to said base support member about said base support outlet so that the gaseous medium passing through said base support outlet passes through said flow control means, said flow control means defining a critical size orifice therein through which the gaseous medium passes to regulate the flow of the gaseous medium therethrough.

* * * * *